United States Patent [19]

Davis, Jr.

[11] Patent Number: 4,946,449
[45] Date of Patent: Aug. 7, 1990

[54] INDWELLING URETHRAL CATHETER SYSTEM AND METHOD

[76] Inventor: Richard C. Davis, Jr., 3384 Tarpon Woods Blvd., Palm Harbor, Fla. 34685

[21] Appl. No.: 943,014

[22] Filed: Dec. 18, 1986

[51] Int. Cl.⁵ .............................................. A61B 19/00
[52] U.S. Cl. ...................................... 604/256; 604/34; 604/101; 128/DIG. 25
[58] Field of Search ............... 604/256, 247, 250, 275, 604/280, 283, 27, 30, 34, 49, 54, 96–103; 128/DIG. 25

[56] References Cited

U.S. PATENT DOCUMENTS

| | | | |
|---|---|---|---|
| 274,447 | 3/1883 | Kennish . | |
| 3,331,371 | 7/1967 | Rocchi et al. | 128/349 |
| 3,379,197 | 4/1968 | Hayes | 128/349 |
| 3,421,509 | 1/1969 | Fiore | 604/280 |
| 3,438,375 | 4/1969 | Ericson | 128/349 |
| 3,503,400 | 3/1970 | Osthagen et al. | 128/349 |
| 3,565,078 | 2/1971 | Vailliancourt | 604/256 |
| 3,585,996 | 6/1971 | Reynolds et al. | 604/158 |
| 3,768,102 | 10/1973 | Kwan-Gett et al. | 3/1 |
| 3,769,981 | 11/1973 | McWhorter | 128/349 |
| 3,805,794 | 4/1974 | Schlesinger | 128/349 |
| 3,810,259 | 5/1974 | Summers | 3/1 |
| 3,811,450 | 5/1974 | Lord | 128/349 |
| 3,812,841 | 5/1974 | Isaacson | 128/DIG. 25 |
| 3,924,634 | 12/1975 | Taylor et al. | 128/349 |
| 3,977,408 | 8/1976 | MacKew | 128/349 |
| 4,026,298 | 5/1977 | Grausz | 128/349 |
| 4,062,363 | 12/1977 | Bonner, Jr. | 128/349 |
| 4,350,161 | 9/1982 | Davis, Jr. | 128/349 |
| 4,432,757 | 2/1984 | Davis, Jr. | 604/99 |
| 4,571,241 | 2/1986 | Christopher | 604/247 |

Primary Examiner—Stephen C. Pellegrino
Assistant Examiner—Denise W. DeFranco
Attorney, Agent, or Firm—Griffin, Branigan & Butler

[57] ABSTRACT

An indwelling urethral catheter system and method of its use involve a drainage shaft (16) mounted in a urinary tract (24) having an externally-operated, normally-closed, fluid valve (38) mounted therein near the meatus (22) of the urinary tract. A removable insertion conduit assembly (12), separate from the catheter drainage shaft, is for extending from outside the body, through the meatus of the urinary tract to plug into the proximal end of the catheter drainage shaft and impinge on the valve for holding it open to allow free drainage through the valve. Once the insertion conduit is removed from the urinary tract it no longer impinges on the valve for holding it open and the valve is thereafter normally closed unless opened by application of force from outside the body.

15 Claims, 2 Drawing Sheets

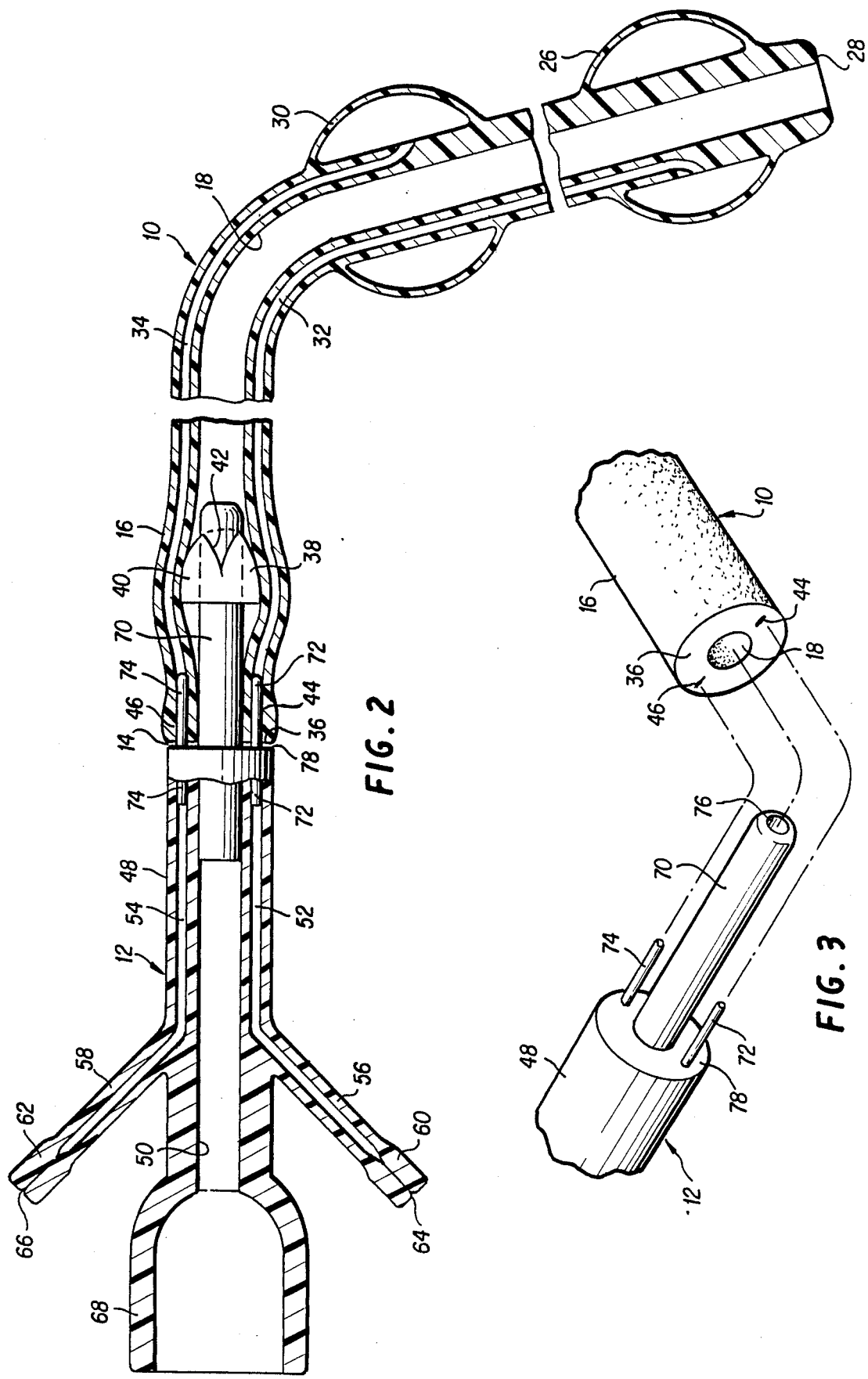

INDWELLING URETHRAL CATHETER SYSTEM AND METHOD

BACKGROUND OF THE INVENTION

This invention relates broadly to the art of urethral drainage catheters, and more particularly to such catheters having valves therein operated from outside of the body.

Discharge of bladder contents can be a source of serious and distressing problems for persons whose natural anatomy is temporarily, or over a longer period of time, incapable of completely controlling the outflow of urine. A traditional urethral balloon catheter of a well known type comprises a flexible tube which extends from outside the body along the urethra into the bladder. More recently, urethral balloon catheter systems have been developed including normally-closed valves in the catheters which can be opened by applying outside forces to the valve to control the flow of urine. Such a valve system is disclosed in U.S. Pat. Nos. 4,350,161 and 4,432,757 to Davis. Although the Davis valved catheter, which is anchored completely inside the urinary tract offers many advantages to persons with impared thinking and/or muscle ability, it is not sufficient in those situations where users thereof cannot apply the necessary external forces to manipulate the valve. Such a situation arises when a person undergoes major surgery, such as open heart surgery, in which he is asleep for a number of hours, and even after waking is usually incoherent. In major-surgery situations, patients are often incontinent for as many as three or four days thereafter and often for the first one or two days after the surgery they are totally incapable of applying forces to activate valves located in urinary tracts In any case it is often desirable to monitor urine production of such patients the first few days after the surgery. Usually, traditional urethral balloon catheters are used in these major surgery situations which allow urine to continuously drain through main lumens into bags located outside the patients. A major disadvantage arising from a drainage lumen extending outside of a body over a period of time is that bacteria spreads along the main lumen into the bladder and ultimately to the kidney In this respect, after only a day of a tube extending from outside of a body into a bladder bacteria has begun to move into the bladder through the tube. One can expect to get an infection if the catheter is left extending outside of the body for four days and frequently such infections are major. One of the purposes of the Davis catheter described in U.S. Pat. Nos. 4,432,757 and 4,350,161 is to avoid a tube which extends outside of the body, therefore allowing the body's natural protective mechanisms operating at the meatus of the urinary tract (such as the fossa navicularis for males which produces antibodies) to prevent bacteria from entering the urinary tract.

Although the Davis catheter of the above-described patents could be used for a patient after one or two days following a major surgery, that is once the patient becomes lucid and active, during the first day after surgery that catheter is not appropriate because it is desirable to continually monitor the flow of urine and the patient is usually not capable of sensing the need for, nor activating the valve for, evacuating urine. For these reasons, the Davis urethral valved catheter described in the above patents, without further improvements, cannot practically be used for such post-surgery patients.

Another shortcoming of the valved catheters of the prior art, such as that described by Davis in U.S. Pat. Nos. 4,432,757 and 3,977,408, is that a clot or some other material passing through a urinary tract might clog the urinary tract, including the valve. Thus, it is an object of this invention to provide a method and apparatus for irregation of the urinary tract to thereby drive clots out of a urinary tract back up into a bladder where they can be dissolved before passing out through the urinary tract.

It is an object of this invention to provide a catheter system and method employing an insertable, urethral catheter which freely drains a patient's bladder but which can also be adjusted to allow selective drainage thereof.

It is a further object of this invention to provide a catheter system and method which has the features of the catheter described in U.S. Pat. Nos. 4,432,757 and 3,977,408 to Davis but which has the added feature of allowing the catheter to be used as a free drainage catheter.

It is a further object of this invention to provide such a catheter system and method which inhibits infection to a much greater degree than do most free-flow urinary catheters.

SUMMARY

According to principles of this invention, an indwelling urethral catheter system having a catheter drainage shaft with a normally-closed valve therein and fully mountable in a urinary tract also includes a removable insertion conduit which is separate from the drainage shaft but which has an elongated connector stint for fitting into a drainage canal of the catheter drainage shaft to impinge on the valve and thereby hold the valve open to allow a continuous drainage flow through the drainage canal of the catheter drainage shaft. When the removable insertion conduit is removed from a meatus of the urinary tract thereby removing the stint from the drainage canal of the drainage shaft, the valve can be selectively opened by application of force from outside of the body.

BRIEF DESCRIPTION OF THE DRAWINGS

The foregoing and other objects, features and advantages of the invention will be apparent from the following more particular description of the preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 2 is a segmented enlarged side sectional view of important features of the indwelling urethral catheter system of FIG. 1;

FIG. 3 is an exploded isometric view of an interface portion of the catheter system of FIGS. 1 and 2 showing interface portions of a catheter drainage shaft and a removable insertion conduit;

DESCRIPTION OF THE PREFERRED EMBODIMENT

Figure 1:
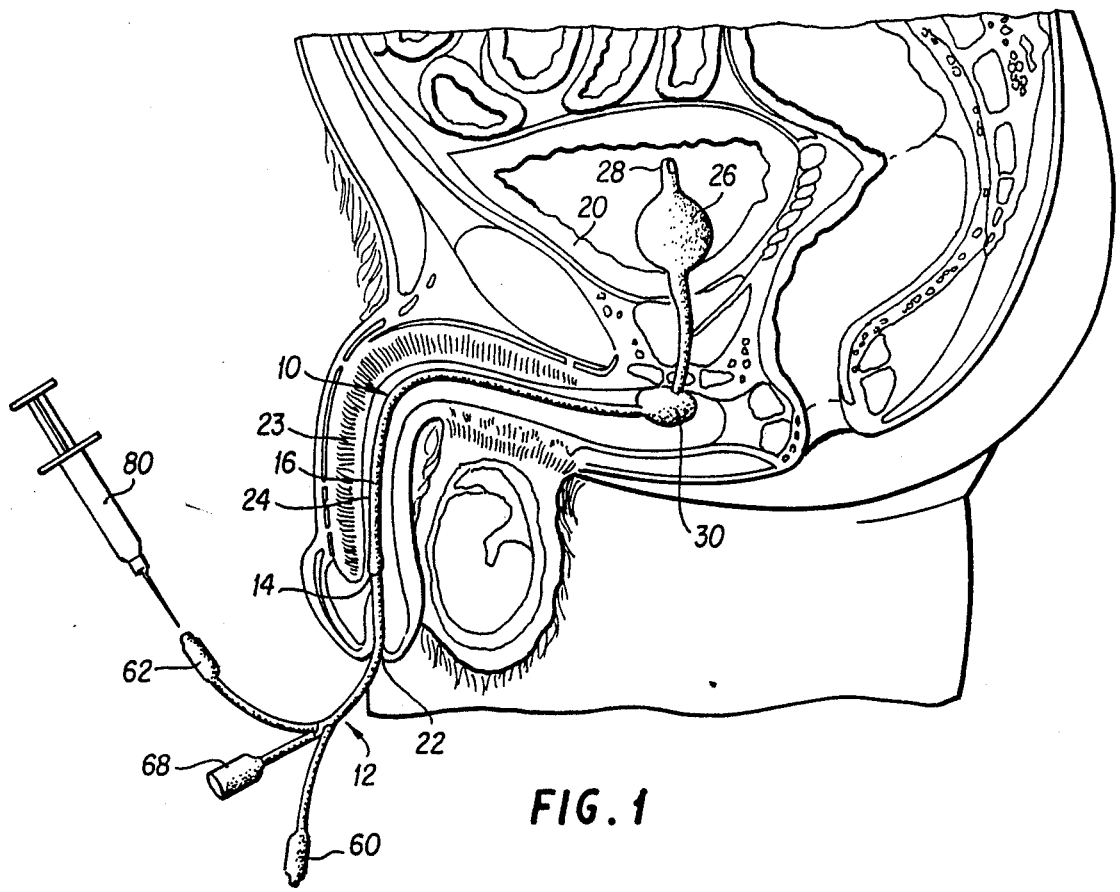
FIG. 1 is a modified sectional view of a male human body showing a penis with an indwelling urethral catheter system of this invention being used therewith.

The indwelling urethral catheter system of this invention comprises basically an indwelling urethral catheter 10 and a removable insertion conduit assembly 12. These two members are shown interfacing one another at 14 in both FIGS. 1 and 2.

The indwelling urethral catheter assembly 10 is quite similar to the catheter of U.S. Pat. Nos. 4,350,161 and 4,432,757 with the exceptions being described herein. The indwelling urethral catheter assembly 10 comprises a catheter drainage shaft 16 which defines an elongated, enclosed drainage canal 18 (FIG. 2) to extend from a human bladder 20 (FIG. 1) to the interface 14 which is near to, however inside, a meatus 22 of a urinary tract 24. In this respect, in FIG. 1, the catheter assembly 10 is shown in a male urinary tract in which the meatus 22 is the meatus of a penis. The catheter assembly also includes a bladder balloon 26 located adjacent its distal end 28 and an inflatable urethra cuff 30 which is also near the distal end 28 but somewhat more proximal along the catheter drainage shaft 16 then the bladder balloon 26. The bladder balloon 26 is quite a bit larger than the urethral cuff 30, being expandable in one case to a size of 10 cc's as opposed to the urethral cuff which is inflatable to a size of 3 cc's. With regard to inflating the bladder balloon 26 and the urethral cuff 30, a balloon inflation lumen 32 and a cuff inflation lumen 34 respectively extend from the interior of the bladder balloon 26 and the urethral cuff 30 through the wall of the catheter drainage shaft 16 to a proximal end 36 thereof.

Mounted in the drainage canal 18 of the catheter drainage shaft 16, near its proximal end 36, is a normally-closed mitre valve 38. The mitre valve 38 is not shown cut-away in FIG. 2, however, it is in FIGS. 4 and 5. The valve comprises a soft rubber (or other elastic substance), dome-shaped diaphragm 40 directed in an upstream direction. In a center of the dome-shaped diaphragm 40 is a slit incision, 42 which evenly divides the dome. This slit is shown to be closed in FIG. 4 so that liquid coming from the distal, or upstream direction cannot find passage through the valve as any pressure from that side tends to compress the dome-shaped diaphragm and close the incision 42. However, pressure or objects coming upstream from the proximal, or downstream end tend to open the slit 42 without damaging the valve and the purpose in this will be described in more detail below.

At the proximal end 36 of the balloon inflation lumen 32 and the cuff inflation lumen 34 the wall of the catheter drainage shaft 16 forms natural rubber seals 44 and 46. In this respect, these natural rubber seals 44 and 46 are constructed to seal the proximal openings of the balloon and cuff inflation lumens 32 and 34 unless a pin or the like is inserted therethrough to temporarily hold them open.

Describing next the removable insertion conduit assembly 12, this member includes a conduit 48 defining a conduit drainage passage 50. The conduit 48 has approximately the same cross sectional circumference as that of the catheter drainage shaft 16 so that both of these members can be inserted into a urethera of a human body, as shown in FIG. 1. The wall of the conduit 48 forms respectively a conduit balloon inflation lumen 52 and a conduit cuff inflation lumen 54. A balloon inflation spur 56 and a cuff inflation spur 58 respectively provide extensions of the conduit balloon inflation lumen 52 and the conduit cuff inflation lumen 54 and form respectively seal valves 60 and 62 at a balloon inflation port 64 and a cuff inflation port 66. A receptor end 68 allows attachment to a receptor for receiving urine passing through the drainage canal 18 of the catheter drainage shaft 16 and the conduit drainage passage 50 of the conduit 48.

Forming a part of the removable insertion conduit assembly 12 are a drainage connector stint 70, a balloon inflation pin 72 and a cuff inflation pin 74, all of which are rigid tubes adhered to the conduit 48. In this respect, the drainage conduit stint 70 is adhered in the conduit drainage passage 50 so that a bore 76 thereof is in communication with the conduit drainage passage 50. Similarly, the balloon inflation pin 72 is adhered in the conduit inflation lumen 52 so that its bore is in communication therewith and the cuff inflation pin 74 is adhered in the conduit cuff inflation lumen 54 so that its bore is in communication therewith. The drainage connector stint 70, the balloon inflation pin 72, and the cuff inflation pin 74, all project outwardly from the distal end 78 of the conduit 48, with the drainage connector stint 70 projecting sufficiently that when it is fully inserted into the proximal end of the drainage canal 18 of the catheter drainage shaft 16 it extends through and past the mitre valve 38. With such engagement the outer surface of the stint 70 is in sealing contact with the valve 38 and the surfaces of the drainage canal 18 to prevent flow of urine therebetween. The balloon inflation pin 72 and the cuff inflation pin 74 project outwardly sufficiently far to hold open the natural rubber seals 44 and 46 at the proximal ends of the balloon and cuff inflation lumens 32 and 34.

With regard to materials of which the indwelling urethral catheter system described herein is made, preferably silastic rubber compounds, or other state-of-the-art biological inert resilient materials are used for constructing the indwelling urethral catheter assembly 10 as well as most of the removable insertion conduit assembly 12. However, the drainage connector stint 70 and the balloon and cuff inflation pins 72 and 74 must be rigid, and can therefore be made of a rigid, biologically-inert plastic or metal. The mitre valve 38, the bladder balloon 26, and the urethral cuff 30 can be made of a different material from the catheter drainage shaft 16, although, these members must be integrated together by an adhesive or in some other manner. Natural rubber has been found to provide appropriate sealed openings such as the rubber seals 44 and 46 an the seal valves 60 and 62. The conduit 48 can be rigid or semi-rigid or even rather flexible.

Turning now to operation of the indwelling urethral catheter system and the method of using the device of this invention, when the system is to be inserted into the urinary tract of a patient, the distal end of the removable insertion conduit assembly 12 is plugged into the proximal end of the indwelling urethral catheter assembly 10 as is depicted in FIGS. 1 and 2. That is, the drainage connector stint 70 is inserted into the drainage canal 18 and extends a sufficient distance for passing through the slit 42 of the mitre valve 38 so that the outer end of the stint bore 76 is on the upstream, or distal, side of the mitre valve 38 and the balloon and cuff inflation pin 72 are inserted through the rubber seals 44 and 46 of the balloon and cuff inflation lumens 32 and 34 so that their bores communicate with these lumens. In FIG. 2 the proximal end 36 of the catheter drainage shaft 16 is shown spaced slightly from the distal end 78 of the conduit 48, however, this is for illustration purposes only and when the system is actually used, these members abut against one another.

Figures 4, 5:
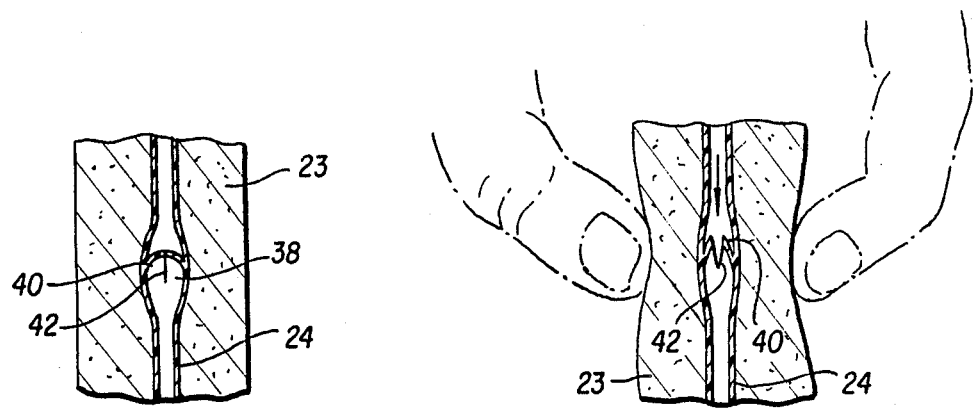
FIG. 4 is a segmented side sectional view of a portion of the catheter system of FIGS. 1 and 2 mounted in a penis showing a mitre valve of FIG. 2 in a closed position; and, FIG. 5 is a view similar to FIG. 4 but showing the mitre valve being opened by fingers applying force to the penis.

The distal end 28 of the catheter drainage shaft 16 is inserted through the meatus 22 of a urinary tract up through the urethra thereof and finally into the bladder 20 so that the balloon 26 is fully in the bladder but so that the urethral cuff 30 remains in a cavity of the urethra. In FIG. 1 it is shown that the urethral cuff 30 is downstream of the prostatic urethra of a male patient which prevents retrograde movement of the catheter drainage shaft 16. In this position, the interface 14 between the urethral catheter assembly 10 and the removable insertion conduit assembly 12 is about an inch inside the meatus 22 of the urinary tract. In a male patient, the interface is upstream of the facca navicularis. Thus, the distal end 78 of the removable insertion conduit assembly 12 is inserted slightly (one inch) into the urinary tract. At this point, the needle of a syringe 80 (FIG. 1) is inserted into the inflation ports 64 and 66 of the seal valves 60 and 62 to inflate the bladder balloon 26 and the urethral cuff 30 via the conduit inflation lumens 52 and 54, bridged by the balloon and cuff inflation pins 72 and 74 to the shaft inflation lumens 32 and 34. When the needle of the syringe 80 is pulled out of the balloon and cuff inflation ports 64 and 66, the natural rubber seals 60 and 62 thereat expand to close these ports and prevent deflation of the bladder ballon 26 and the urethral cuff 30. A receptor is attached to the receptor end 68 for receiving urine drained from the bladder 20 through the drainage canal 18, the bore 76 of the drainage connector stint 70, and the conduit drainage passage 50. In this respect, in this insertion mode the stint 70 bypasses the valve 38 by allowing fluids to pass through its bore 76. When the indwelling urethral catheter assembly 10 is first inserted into a urinary tract, for example immediately after surgery, it is often desirable that free drainage, allowed by this mode, be continue-d for a period of time while the patient is incapable of sensing and controlling urine flow and while it is desirable to monitor the production of urine. However, once it no longer is necessary to monitor the urine and the patient is capable of sensing and performing urine evacuation control, the removable insertion conduit assembly 12 is carefully pulled out of the meatus 22 of the urinary tract, withdrawing the drainage connector stint 70 from the drainage canal 18 and the inflation pins 72 and 74 from the shaft inflation lumens 32 and 34. When this happens, the slit 42 of the normally-closed mitre valve 38 automatically closes, as is depicted in FIG. 4, to prevent further downstream flow of urine. Also, the seals 44 and 46 close to continue to prevent deflation of the bladder balloon 26 and the urethral cuff 30. The catheter assembly is held in place by the bladder balloon 26 and the urethral cuff 30 with the mitre valve 38 being located near the meatus 22 of the urinary tract, and in the mode of FIG. 1, it is located in the penis. Upon sensing the need for urinating the patient operates the valve 38. With regard to operating the valve 38, for a male patient with the embodiment of FIG. 1, he applies pressure on opposite sides of his penis to deform and thereby open the mitre valve 38 as is shown in FIG. 5.

It will be understood by those of ordinary skill in the art that the system and method of this invention provide vast improvements to prior-art valve urethral catheter assemblies in that they allow a single catheter to be used in both a free drain mode and in a selective-valve mode without the removal of the catheter from a urinary tract. Thus, this system and method are ideal for patients recovering from major surgery. Also, it will be understood by those skilled in the art that this invention allows all of the infection-fighting benefits described in U.S. Pat. Nos. 4,350,161 and 4,432,757 to Davis when used in the selective-valve mode. Further, the apparatus and method of this invention allows the irregation of a urinary tract by inserting a conduit assembly stint through a meatus of a urinary tract into the valve of a catheter drainage shaft so that fluid can be driven through the stint, back through the urinary tract to force clots and the like into the bladder where they can be dissolved.

While the invention has been particularly shown and described with reference to a preferred embodiment, it will be understood by those skilled in the art that various changes in form and detail may be made therein without departing from the spirit and scope of the invention.

For example, types of valves other than the mitre valve described and shown herein could be used. It is possible to manufacture the mitre valve separate from the wall of the catheter drainage shaft 16 and then to adhere it in the drainage canal 18.

The embodiments of which an exclusive property or privilege are claimed are defined as follows:

1. An indwelling urethral catheter system for use with a human body comprising:
   a catheter drainage shaft defining an enclosed drainage canal for extending through a urinary tract of the human body to provide urinary drainage therethrough and having distal and proximal ends;
   an anchoring means attached to the catheter drainage shaft near said distal end thereof for holding said drainage shaft in a proper position in said urinary tact;
   a valve means attached to said catheter drainage shaft and being positioned in said drainage canal near said proximal end of said shaft for being in a closed position to prevent flow of urine through said drainage canal but for being selectively moved from said closed position to an open position by applying force thereto from outside the human body for respectively allowing and disallowing fluid flow through said enclosed drainage canal;
   said catheter drainage shaft being of a length, and said anchoring means being located at a position therealong, such that when said catheter drainage shaft is held in said proper position in said urinary tract, said valve means and the proximal end of said drainage shaft are located entirely within said urinary tract yet accessible from outside the human body; and,
   a removable insertion conduit separate from said catheter drainage shaft, said removable insertion conduit defining a drainage passage and having a distal end and a proximal end, said removable insertion conduit including at the distal end thereof an elongated connector stint having a cross-sectional size and a length for fitting into the drainage canal of the catheter drainage shaft from the proximal end thereof and extending from outside the human body into the human body to impinge on said valve means for holding said valve means open;

said valve means having the further function of remaining open in response to engagement with said stint to be held open thereby, but upon removal of said stint from engagement therewith, of being allowed to close to prevent further passage of liquid through said drainage canal;

whereby said catheter drainage shaft can be held in a urinary tract by said anchoring means with its proximal end being positioned in said urinary tract accessible to the meatus thereof to outside the human body and the removable insertion conduit can extend through the meatus of the urinary tract with elongated connector stint inserted into the proximal end of the drainage-shaft drainage canal for engaging said valve and thereby holding said valve open to allow continuous flow of urine past said valve and out through the insertion conduit drainage passage to outside the body and said removable insertion conduit can then be removed from the urinary tract, thereby removing said stint from the drainage canal of said catheter drainage shaft and from said urinary tract for disengaging said valve and allowing it to close but to be selectively opened by a force applied there from outside said body.

2. An indwelling urethral catheter system as in claim 1 wherein said stint is a tube that extends through said valve and which has a bore through which urine located upstream of said valve can flow through said valve.

3. An indwelling urethral catheter system as in claim 2 wherein said anchoring means comprises a bladder balloon attached to said catheter drainage shaft and an expendable urethral cuff attached thereto, said bladder balloon and said urethral cuff being spaced along said drainage shaft and said balloon being inflatable through a lumen passing through said removable insertion conduit and said catheter drainage shaft.

4. An indwelling urethral catheter system as in claim 3 wherein said valve means is a mitre valve comprising a resilient dome-shaped member having a slit therein.

5. An indwelling urethral catheter as in claim 3 wherein said expandable urethral cuff is also inflatable and said removable insertion conduit further includes hollow balloon and cuff inflation pins projecting outwardly at said proximal end of said removable insertion conduit for insertion into inflation lumens formed in the wall of said catheter drainage shaft, and wherein the wall of said catheter drainage shaft includes said inflation lumens whereby when said stint extends into said drainage canal of said catheter drainage shaft said pins extend into said inflation lumens of said catheter drainage shaft wall through said cuff and said balloon can be inflated.

6. An indwelling urethral catheter as in claim 2 wherein said valve means is a mitre valve comprising a resilient dome-shaped member having a slit therein.

7. An indwelling urethral catheter as in claim 1 wherein said anchoring means comprises a bladder balloon attached to said catheter drainage shaft and an expandable urethral cuff attached thereto, said bladder balloon and said urethral cuff being spaced along said drainage shaft and said balloon being inflatable through lumens passing through said removable insertion conduit and said catheter drainage shaft for respectively inflating in a bladder and a urethra.

8. An indwelling urethral catheter as in claim 7 wherein said valve means is a mitre valve comprising a resilient dome-shaped member having a slit therein.

9. An indwelling urethral catheter as in claim 1 wherein said valve means is a mitre valve comprising a resilient dome-shaped member having a slit therein.

10. A method for inserting and using an indwelling urethral catheter comprising the steps of:

inserting a catheter drainage shaft in a urinary tract, said catheter drainage shaft defining an enclosed drainage canal to provide urinary drainage through the urinary tract from a bladder, in which the distal end of the drainage shaft is located, to a point downstream thereof in the urinary tract at which a proximal end of the drainage shaft is located, said drainage shaft including an anchoring means for holding said drainage shaft in a proper position in the urinary tract and a valve means positioned in the drainage canal for being in a closed position to prevent flow of urine through said drainage canal but for being selectively opened by applying forces thereto from outside the human body for allowing fluid flow through the said drainage canal, said catheter drainage shaft being of a length, and said anchoring means being located at a position therealong, such that when said catheter drainage shaft is held in the proper position in the urinary tract said valve means and the proximal end of said drainage shaft are located in said urinary tract, but accessible from a meatus thereof from outside the human body;

inserting a removable insertion conduit, which is a separate member from the catheter drainage shaft, through the meatus of the urinary tract, to extend from the meatus of the urinary tract into the catheter-drainage-shaft drainage canal, said removable insertion conduit having at its distal end an elongate connector stint which is inserted into the drainage canal of the catheter drainage shaft to extend to and impinge on said valve means for holding said valve means open;

allowing urine to flow freely from said bladder through said drainage shaft and through said valve to outside the body;

pulling said removable insertion conduit from said urinary tract thereby pulling said elongated connector stint from said drainage canal of said catheter drainage shaft to thereby allow said valve means to move to a closed position and thereby prevent urine flow through said valve means; and thereafter, selectively opening said valve means by applying forces thereto from said body for allowing selective flow of urine through the meatus of said urinary tract.

11. A method as in claim 10 wherein said stint is tubular in shape, having a bore, and wherein said step of allowing urine to flow freely through said valve includes the substep of draining said urine through a bore in said stint.

12. A method as in claim 11 wherein said valve is a mitre valve comprising a resilient dome having a slit therein and said step of inserting said stint through said valve includes the substep of inserting said stint through said slit in said dome.

13. A method as in claim 10 wherein said anchoring means comprises a bladder balloon and an inflatable urethral cuff attached to said catheter drainage shaft along the length thereof, said bladder balloon and said urethral cuff being spaced from one another with said bladder balloon being located close to the distal end of said drainage shaft and being inflated in a bladder and said cuff being inflated in the urethra during said step of inserting said catheter drainage shaft in said urinary tract.

14. A method as in claim 10 wherein the distal end of said removable insertion conduit is inserted into the drainage canal of the catheter drainage shaft before said catheter drainage shaft is inserted into the urinary tract so that they are inserted into the urinary tract together.

15. An indwelling urethral catheter as in claim 3 wherein said removable insertion conduit further includes a hollow balloon inflation pin projecting outwardly at said proximal end of said removable insertion conduit for insertion into an inflation lumen formed in the wall of said catheter draining shaft, and wherein the wall of said catheter drainage shaft includes said inflation lumen, whereby when said stint extends into said drainage canal of said catheter drainage shaft said pin extends into said inflation lumen of said catheter drainage shaft wall through which said cuff and said balloon can be inflated.

* * * * *